United States Patent [19]
Maekawa et al.

[11] Patent Number: 5,159,398
[45] Date of Patent: Oct. 27, 1992

[54] FLOW IMAGING CYTOMETER

[75] Inventors: Yasunori Maekawa; Tokihiro Kosaka, both of Hyogo, Japan

[73] Assignee: TOA Medical Electronics Co., Ltd., Hyogo, Japan

[21] Appl. No.: 755,549

[22] Filed: Sep. 5, 1991

[30] Foreign Application Priority Data

Feb. 27, 1991 [JP] Japan .................................. 3-33138

[51] Int. Cl.$^5$ ..................... G01N 33/48; G01N 21/64; G06K 9/20
[52] U.S. Cl. .................... 356/73; 250/461.2; 356/39; 356/417; 356/23; 382/6
[58] Field of Search ..................... 356/39, 72, 73, 318, 356/417, 23; 250/461.2; 382/6

[56] References Cited

U.S. PATENT DOCUMENTS

| | | | |
|---|---|---|---|
| 3,992,112 | 11/1976 | Adrion | 356/39 |
| 4,338,024 | 7/1982 | Bolz et al. | 356/23 |
| 4,786,165 | 11/1988 | Yamamoto et al. | 356/23 |
| 5,093,866 | 3/1991 | Hamilton et al. | 382/6 |

Primary Examiner—Vincent P. McGraw
Attorney, Agent, or Firm—Pearne, Gordon, McCoy & Granger

[57] ABSTRACT

A white-light image and a fluorescent image are capable of being captured by a single video camera, and a single light source for producing exciting light is used to pick up the fluorescent image and monitor arrival of particles to the image capturing area. Specifically, besides a strobe light source, a light source, the output of which normally is low, is provided for exciting fluorescence and for monitoring cell flow-through. An image intensifier is used in the light-receiving system of the fluorescent image and is supplied with a voltage the size and timing of which are controlled in such a manner that the irradiation of a cell with the strobe light when the white-light image is captured will not have an adverse effect upon the aforementioned light-receiving system. This makes it possible to pick up two images each in a different zone on the light-receiving surface of image capturing means.

5 Claims, 4 Drawing Sheets

FLOW IMAGING CYTOMETER

BACKGROUND OF THE INVENTION

1. Field of the Invention

This invention relates to a flow imaging cytometer. More particularly, the invention relates to a flow-imaging particle analyzing system in which cells fluorescently stained in a manner suitable for the particular cells of interest are introduced to a flow cell to be formed into a planar sheathed flow and irradiated with white light (strobe light) to obtain a white-light image and excited with laser light to obtain a fluorescent image in a highly efficient manner, and in which the two types of images can be captured simultaneously by a single video camera and subject to analysis.

2. Description of the Prior Art

Attempts have been made to irradiate cells, which have been stained and smeared on a glass slide, with light such as visible light or ultraviolet light under a microscope, capture a fluorescent image of cells of interest, analyze the resulting image and obtain physiological information relating to the cells. However, a method of this kind is not suited to the analytical processing of a large number of cells in a short time, and analysis using fluorescent images has only limited application.

In another example of the conventional flow imaging cytometer, the cell information is obtained using a gross value of the fluorescence emitted from the fluorescently stained cell. In other words, the fluorescence emitted from each portion of the cell is integrated over the entirety of the cell, and the cell information is obtained in the form of such an integrated value. Though such a method lends itself to analysis of a large number of cells in a short period of time, it is not possible to acquire detailed information as to which portions of individual cells have been stained and caused to emit fluorescence. Consequently, this method is limited in terms of analytical performance.

On the other hand, a cell classifying apparatus that has been put into practical use employs a technique in which cells stained in a manner suitable for a particular cell of interest are introduced to a flow cell to be formed into a planar sheathed flow and irradiated with strobe light, a still picture is obtained by a video camera and image processing is applied. However, the state of the art is such that the capturing and analysis of fluorescent images of individual cells using this method have still not reached a practical stage because of problems related to fluorescent imaging sensitivity. The present invention makes use of the technology employed in a flow imaging cytometer of the type having a high image capturing efficiency, as previously proposed in the specification of Japanese Patent Application No. 185794/1990.

SUMMARY OF THE INVENTION

Thus, the art still lacks a definitive flow-imaging particle analyzing system for sensing cells that pass through an image capturing area and irradiating the cells with concentrated exciting light, thereby to assure the required flourescent intensity and obtain a fluorescent image, and for subjecting the fluorescent image, as well as a white-light image of the cells derived from the conventional white-light source, to highly efficient image capturing and analysis using a single video camera.

Accordingly, an object of the present invention is to provide a flow imaging cytometer which expands upon the idea of the previously proposed (the aforementioned Japanese Patent Application No. 185794/1990, hereinafter referred to as "the earlier application") flow imaging cytometer of the type having a high image capturing efficiency, wherein fluorescence emitted by a fluorescently stained cell as a result of irradiating the cell with laser light is obtained, by single video camera, as a two-dimensional image at the same time as a white-light image acquired by conventional strobe-light (white-light) irradiation.

According to the present invention, the foregoing object is attained by providing a flow imaging cytometer comprising a flow cell formed to include a flat flow path for causing a specimen solution containing particle components to be sensed to flow as a flat stream, a first light source arranged on a first side of the flow cell for irradiating the specimen solution in the flow cell with light the quantity of which is switched, a second light source arranged on the first side of the flow cell for irradiating the specimen solution in the flow cell with pulsed light, first image capturing means arranged on a second side of the flow cell for capturing still pictures of particle components in the specimen solution irradiated with high-luminance pulsed light from the first light source particle components irradiated with the light from the second light source, second image capturing means arranged on the second side of the flow cell for capturing still pictures of particle components in the specimen solution the first light source, processing means for executing prescribed analysis based upon image data from the first and second image capturing means; and control means for detecting the particle components based upon the image data from the second image capturing means; and on the basis of such detection, first for switching the first light source over to irradiation with the high-luminance light, and then operating the second light source following a prescribed delay, within an image capturing period of the first image capturing means, wherein the first light source is a light source for exciting fluorescence, and the image resulting from the first light source and the image resulting from the second light source are each captured in a different area on a light-receiving surface of the first image capturing means.

The flow imaging cytometer of the present invention is further characterized in that the first image capturing means has a two-dimensional image capturing area on the flow of the specimen solution, the second image capturing means has a linear image capturing area on the flow of the specimen solution, the image capturing area of the second image capturing means is formed so as to cross the flow of the specimen solution within the image capturing area of the first image capturing means, the image capturing area of the first image capturing means is divided into a zone which includes, and a zone which does not include, the image capturing area of the second image capturing means, and an image in one of these zones resulting from irradiation with the high-luminance light from the first light source and an image in the other of these zones resulting from irradiation by the second light source are captured by the first image capturing means.

The flow imaging cytometer of the present invention is further characterized by having masking means for interrupting light on the optic path of the first image capturing means in such a manner that the two images do not overlap each other on the light-receiving surface of the first image capturing means.

The flow imaging cytometer of the present invention is further characterized by having means forming for irradiating light from the first light source into an elongated elliptical shape, and in that the light-receiving system of a fluorescent image is provided with an image intensifier, and the image intensifier is operated only when the fluorescent image is captured.

Other features and advantages of the present invention will be apparent from the following description taken in conjunction with the accompanying drawings.

DETAILED DESCRIPTION OF THE PREFERRED EMBODIMENTS

A preferred embodiment of a flow image cytometer according to the present invention will now be described with reference to the drawings.

Figure 1:
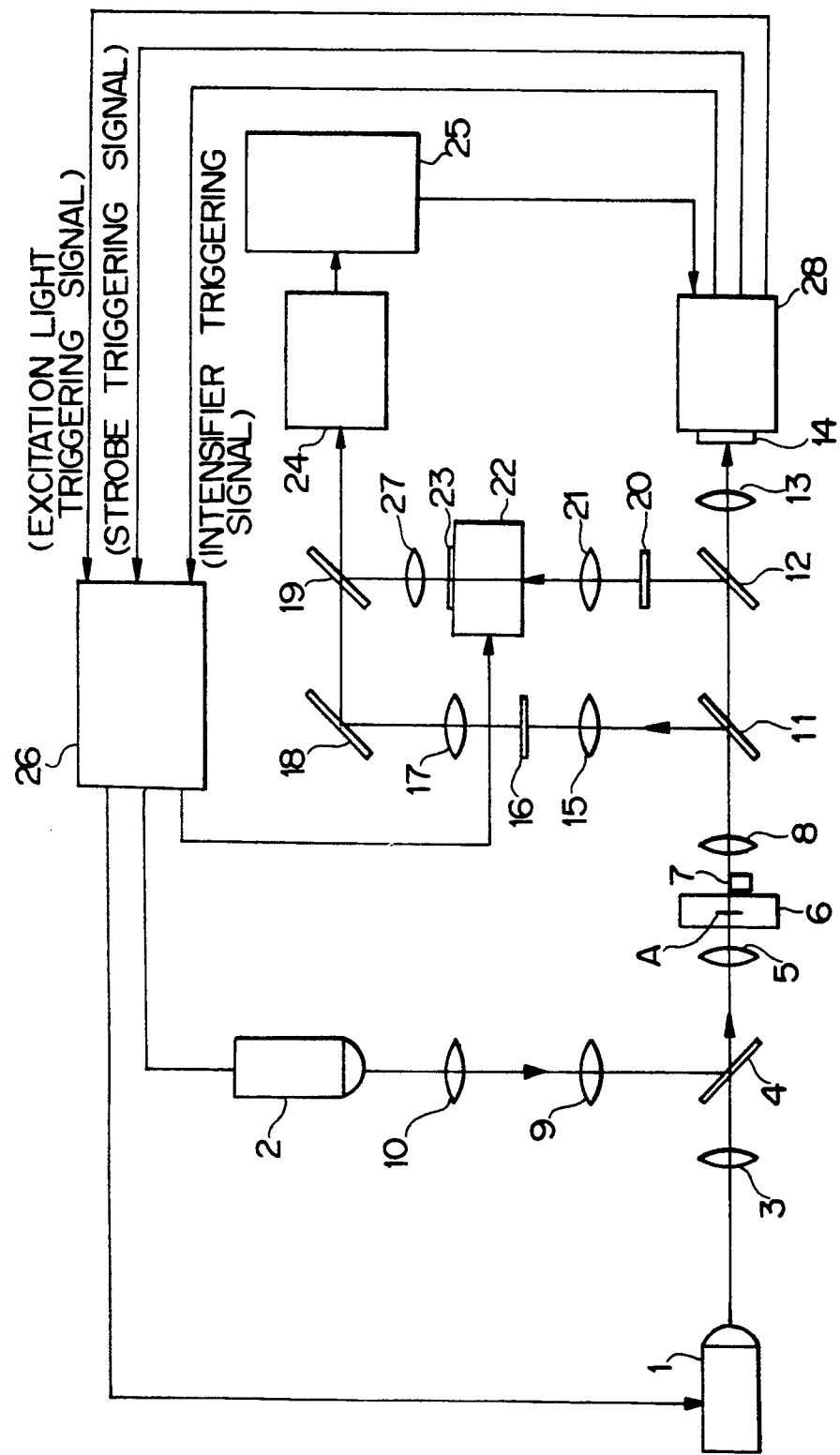
FIG. 1 is a block diagram illustrating the construction of a flow imaging cytometer according to the present invention.
Figure 2:
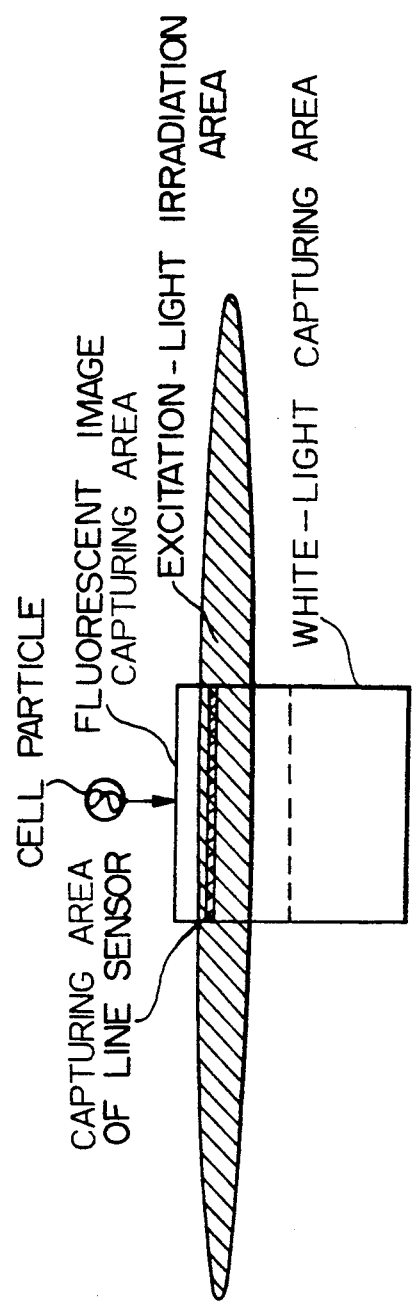
FIG. 2 is an explanatory view illustrating an example of light-irradiating areas and image capturing areas of the flow cell shown in FIG. 1.

As illustrated in FIG. 1, the flow imaging cytometer includes a laser light source 1 (e.g. an He-Cd laser) for exciting fluorescence and also for monitoring the passage of cells through the cytometer, and a strobe 2 serving as a light source for white-light photography. Unlike the strobe light source 2, the laser light source 1 is adapted to irradiate an image capturing area constantly in order to monitor cell flow-through. The light from laser 1 is stopped down to a finely elongated beam spot perpendicular to the direction of cell travel by a cylindrical lens 3 and a condenser lens 5 and irradiates an image capturing area of a line sensor 14, as illustrated in FIG. 2. The reason for this is to obtain a more uniform light intensity and to improve the S/N ratio when a fluorescent image is captured. In this embodiment, the image capturing area of the line sensor 14 is provided slightly above mid-center of the upper half of the generally rectangular image capturing area of video camera 24, as shown in FIG. 2.

The light from the laser 1 leaving the image capturing area passes through an objective lens 8 and is then split by a beam-splitter 11. Part of the light from the beam-splitter 11 passes through a dichoric mirror 12 and enters to a projecting lens 13, which proceeds to form an image on the line sensor 14. The line sensor 14 successively produces voltage outputs conforming to the accumulated amount of photoelectrical conversion of each pixel exposed for a scanning period (several tens of microseconds) of one line. By means of signal processing similar to that set forth in the earlier application, triggers irradiation by exciting light and for fluorescent image capturing are applied when a cell crosses the image capturing area of the line sensor 14 during even-numbered field intervals of the video camera 24.

Figure 4:
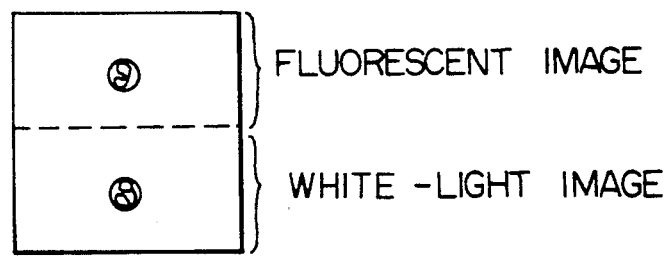
FIG. 4 is a diagram showing an example of an imaged frame of a cell captured by a video camera.

The time from the instant a cell crosses the image capturing area of the line sensor 14 until the cell is irradiated with the exciting light is 100–200 $\mu$sec if the scanning period of the line sensor 14 is 50 $\mu$sec. On the assumption that the flow velocity of cells in flow cell 6 is 30 mm/sec, a cell will move 3–6 $\mu$m in this period of time. Accordingly, the image of a cell obtained by being irradiated with the exciting light can always be acquired in the area located in the upper half of one imaged frame, as illustrated in FIG. 4. The laser 1 usually delivers a small output power to monitor passage of cells through the flow cell, but the laser is caused to generate high-luminance pulses when fluorescent images are captured.

Fluorescence emitted by a cell in response to irradiation with the exciting light passes through the objective lens 8 and the beam-splitter 11 to be reflected by the dichroic mirrors 12. The exciting light which has passed through the image capturing area is intercepted by a beam stopper 7, and stray light is removed by the filter 20. Near infrared light constantly emitted in order to monitor cell flow-through also is eliminated by a filter 20.

The fluorescent light which has passed through the filter 20 enters to a projecting lens 21, whereby an image intensifier 22. At this time a high-voltage is applied to the image intensifier 22 so that the image is intensified by a factor of $10^3$–$10^6$ by an internal MCP (a microchannel plate) to form an image on the fluorescent output surface of the intensifier. This image, half of which is masked by a semicircular mask 23, is acted upon by a projecting lens 27 and a half-mirror 19 so that an image is formed on only half of a CCD area sensor of the video camera 24.

Meanwhile, the fluorescent light reflected by the beam-splitter 11 impinges upon a projecting lens 15, which forms an image on a semicircular mask 16. This image, however, is blocked by the mask.

After transmission of the signal for triggering irradiation with the exciting light, strobe irradiation is triggered following a suitable time delay. This time delay should be so selected that strobe irradiation is triggered when a cell of interest has reached the lower half of the image capturing area of video camera 24. The strobe triggering signal applied to a light-source power supply 26 is produced by a power-supply controller 28, which functions also a discriminator for cell flow-through.

Figure 5:
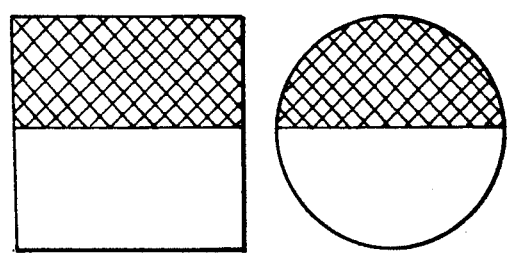
FIG. 5 is a diagram showing examples of semicircular and rectangular masks associated with the set-up of FIG. 1.

In operation, the light from strobe 2 is collimated by a collimator lens 10, the collimated light passes through a condenser lens 9 and a dichroic mirror 4 and enters to the condenser lens 5, by virtue of which substantially the entirety of the image capturing area of video camera 24 is irradiated with the strobe light uniformly. This strobe light which has passed through the image capturing area is reflected by the beam-splitter 11 upon being acted upon by the objective lens 8. The reflected light impinges upon the projecting lens 15. The latter forms an image upon the semicircular mask 16, shown in FIG. 5. The upper half of the image is blocked by the mask 16, as a result of which an image is formed on only half of a CCD area sensor of the video camera 24 via a projecting lens 17, a mirror 18 and the half-mirror 19.

The part of the light reflected by the dichroic mirror 12 upon passage through the beam-splitter 11 passes through the filter 20 and the projecting lens 21, whereby an image is formed on the photoelectric surface of image intensifier 22. However, since gating is applied in such a manner that a negative voltage is impressed upon the image intensifier 22 at this point in time, an image does not appear on its fluorescent surface. (In other words, the shutter of the intensifier is closed.) A gating signal for this purpose is produced by the discriminator/power-supply controller 28 which, as mentioned above, is for judging when a cell has passed through the image capturing area, and for controlling the light sources.

Figure 3:
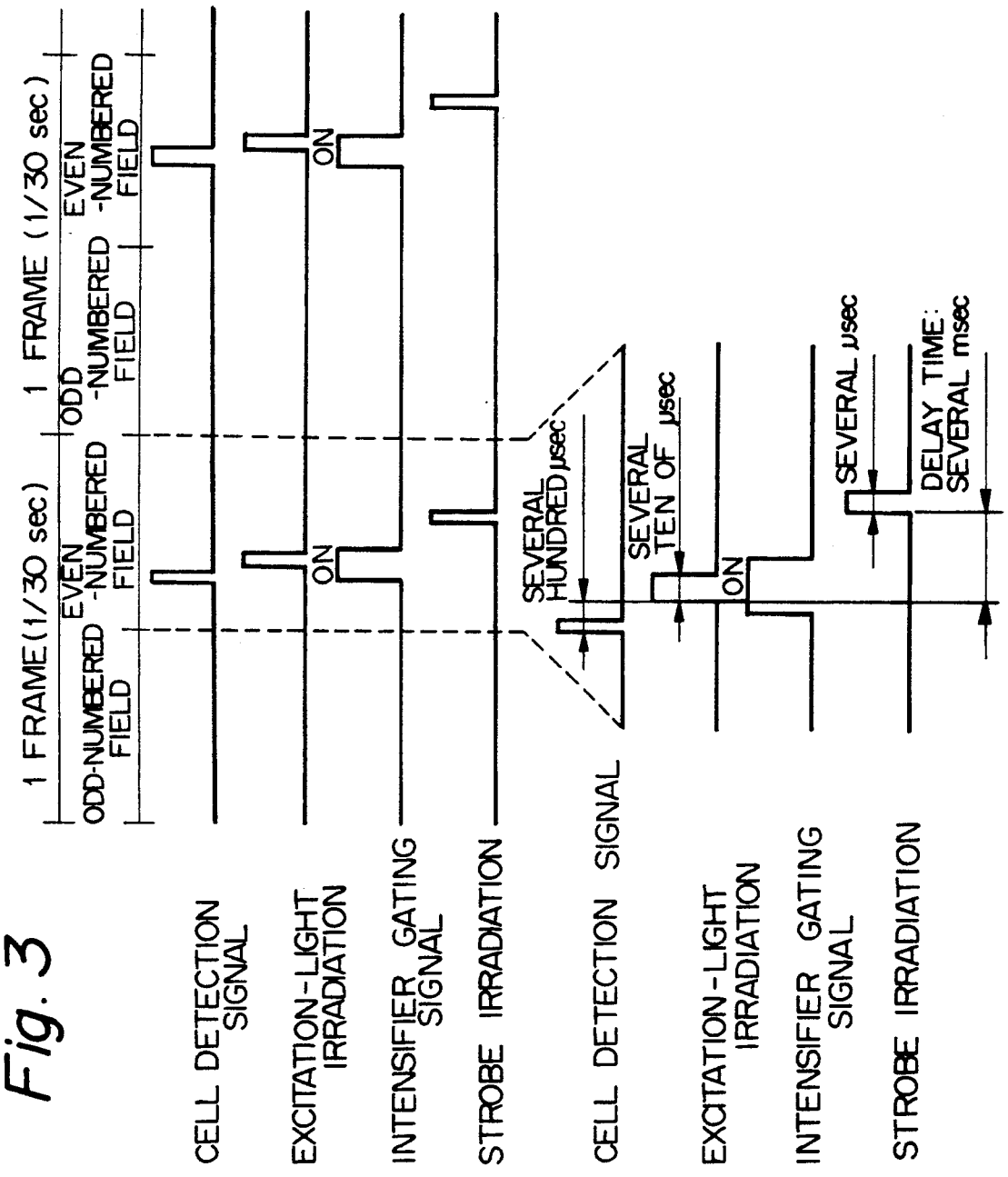
FIG. 3 is a timing chart illustrating irradiation timing and the timing of a grating signal for an image intensifier.

FIG. 3 is an example illustrating the timing of exciting-light emission, strobe-light emission and the timing of gating signals for the image intensifier 22 after detection of a cell passing through the image capturing area. The signals for controlling such timing are produced by the discriminator/controller 28 shown in FIG. 1.

In accordance with the above sequence, the fluorescent image and white-light image of a cell can be captured by a single video camera after the cell has passed through the image capturing area.

It will suffice if the time delay from the moment the cell flows through the image capturing area of line sensor 14 to the moment the cell is irradiated with the strobe light is fixed so long as the flow velocity of the cell can be made constant. If there is the possibility that flow velocity will fluctuate, however, the following expedient can be adopted. Specifically, the position at which the white-light image of the cell appears in the image capturing area can readily be determined by image processing executed by an image analyzer 25. Therefore, if this position shifts from the expected position, feedback control is applied so as to correct the time delay which elapse until irradiation with the light from strobe 2 is performed.

In another embodiment, the positions at which the white-light image light-receiving system and fluorescent image light-receiving system are disposed in FIG. 1 can be interchanged if desired.

The invention as described above affords the following advantages:

(1) Since passage of cells through the image capturing area is monitored all times, the images of cells can be obtained efficiently and with excellent selectivity even if the cell of interest has a low concentration in the specimen under examination.

(2) The irradiating light for obtaining the fluorescent image of a cell need not irradiate the entire image capturing area of the video camera; it can be stopped down to a specific area instead. This makes it possible to raise the intensity of the irradiating light per unit area so that exposure time can be shortened.

(3) Two images, namely the white-light image and the fluorescent image, can be acquired in one imaged frame simultaneously by a single video camera. This facilitates image analytical processing and has advantages in terms of cost.

(4) Since the same laser can be used for monitoring cell flow-through and for exciting fluorescence, the design of the optical system can be simplified and costs reduced.

(5) By using flow imaging cytometry, a high processing capability not feasible with conventional microscopic measurement can be obtained.

As many apparently widely different embodiments of the present invention can be made without departing from the spirit and scope thereof, it is to be understood that the invention is not limited to the specific embodiments thereof except as defined in the appended claims.

What is claimed is:

1. A flow imaging cytometer comprising:

a flow cell formed to include a flat flow path for causing a specimen solution containing particle components to be sensed to flow as a flat stream;

a first light source arranged on a first side of said flow cell for irradiating the specimen solution in said flow cell with light the quantity of which is switched;

a second light source arranged on a first side of said flow cell for irradiating the specimen solution in said flow cell with pulsed light;

first image capturing means arranged on a second side of said flow cell for capturing still pictures of particle components in the specimen solution irradiated with high-luminance pulsed light from said first light source and particle components irradiated with the light from said second light source;

second image capturing means arranged on the second side of said flow cell for capturing still pictures of particle components in the specimen solution irradiated continuously with low-luminance light from said first light source;

processing means for executing prescribed analysis based upon image data from said first and second image capturing means; and control means for detecting the particle components based upon the image data from said second image capturing means, and on the basis of such detection, first for switching said first light source over to irradiation with the high-luminance light, and then operating said second light source following a prescribed delay, within an image capturing period of said first image capturing means;

wherein said first light source is a light source for exciting fluorescence, and the image resulting from said first light source and the image resulting from said second light source are each captured in a different area on a light-receiving surface of said first image capturing means.

2. The flow imaging cytometer according to claim 1, wherein said first image capturing means has a two-dimensional image capturing area on the flow of the specimen solution, said second image capturing means has a linear image capturing area on the flow of the specimen solution, the image capturing area of said second image capturing means is formed so as to cross the flow of the specimen solution within the image capturing area of said first image capturing means, the image capturing area of said first image capturing means is divided into a zone which includes, and a zone which does not include, the image capturing area of the second image capturing means, and an image in one of these zones resulting from irradiation with the high-luminance light from said first light source and an image in the other of these zones resulting from irradiation by said second light source are captured by said first image capturing means.

3. The flow imaging cytometer according to claim 2, further comprising masking means for interrupting light on the optic path of said first image capturing means in such a manner that the two images do not overlap each other on the light-receiving surface of said first image capturing means.

4. The flow imaging cytometer according to claim 2, further comprising means for forming the irradiating light from said first light source into an elongated elliptical shape.

5. The flow imaging cytometer according to any one of claims 1 through 4, wherein a light-receiving system of a fluorescent image is provided with an image intensifier, and said image intensifier is operated only when the fluorescent image is captured.

* * * * *